United States Patent
Murray et al.

(10) Patent No.: US 6,852,891 B2
(45) Date of Patent: Feb. 8, 2005

(54) METHOD OF INHIBITING METHAPHETAMINE SYNTHESIS

(75) Inventors: George M. Murray, Columbia, MD (US); Craig A. Kelly, Ellicott City, MD (US); O. Manuel Uy, Ellicott City, MD (US); Lawrence W. Hunter, Ellicott City, MD (US); David S. Lawrence, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/297,626

(22) PCT Filed: Jun. 21, 2001

(86) PCT No.: PCT/US01/19810

§ 371 (c)(1),
(2), (4) Date: Dec. 9, 2002

(87) PCT Pub. No.: WO02/090316

PCT Pub. Date: Nov. 14, 2002

(65) Prior Publication Data

US 2004/0049079 A1 Mar. 11, 2004

Related U.S. Application Data

(60) Provisional application No. 60/289,461, filed on May 8, 2001.

(51) Int. Cl.⁷ .................. C07D 239/94; C07D 401/12; C07D 403/12; C07D 417/12; C07D 409/12

(52) U.S. Cl. ........................................ 564/381; 252/193
(58) Field of Search ........................... 252/193; 564/381

(56) References Cited

PUBLICATIONS

Database CAPLUS on STN, Acc. No. 1980:127912, Subba et al., Studies in metal–ammonia reduction. Part 2. Influence of ferric ion in the reduction of some alpha–beta–unsaturated ketones, J. of Chem. Research, Synopses (1979), 9, p. 282–3 (abstract).*

* cited by examiner

*Primary Examiner*—Brian Davis
(74) *Attorney, Agent, or Firm*—Francis A. Cooch

(57) ABSTRACT

A method of inhibiting or preventing the use of anhydrous ammonia as a solvent in a dissolving metal reduction process comprises adding to anhydrous ammonia a chemical reagent which is capable of scavenging solvated electrons generated when alkali or alkaline earth metal is dissolved in the anhydrous ammonia, the chemical reagent being added to the anhydrous ammonia such that when alkali metal is dissolved in the anhydrous ammonia containing the chemical reagent and thereafter ephedrine, pseudoephedrine or combination thereof is introduced to the anhydrous ammonia to produce a reaction product, the methamphetamine yield in the reaction product is below 50%, preferably below 10%, and more preferably below 1%. Preferred chemical reagents include Fe(III)citrate, ferrocene, 2-chloro-6-(trichloromethyl)pyridine and 1,1,1,2-tetrafluoroethane.

34 Claims, No Drawings

METHOD OF INHIBITING METHAPHETAMINE SYNTHESIS

CROSS-REFERENCE TO RELATED APPLICATIONS

This application is a national stage filing under 35 USC 371 of International Application No. PCT/US01/19810, filed Jun. 21, 2001, which claims the benefit of prior filed co-pending U.S. Provisional Patent Application No. 60/289,461, filed on May 8, 2001.

STATEMENT OF GOVERNMENTAL INTEREST

This invention was made with Government support under Contract No. N00024-98-D-8124 awarded by the Department of the Navy. The Government has certain rights in the invention.

BACKGROUND OF THE INVENTION

1. Field of the Invention

The present invention relates to a method for inhibiting the synthesis of methamphetamine via the reduction of ephedrine (also known as (−)ephedrine, 1-ephedrine, [1R,2S]-(−)-2-methylamino)-1-phenylpropan-1-ol), or its stereoisomer pseudoephedrine (also known as (+)-P-ephedrine, d-isoephedrine, d-pseudoephedrine, [1S,2S]-(+)-2-[methylamino]-1-phenylpropan-1-ol)). More particularly, this invention relates to the introduction of a chemical reagent into anhydrous ammonia, a common solvent used in the illicit synthesis of methamphetamine (also known as (S)-N,α-dimethylbenzene-ethanamine, (S)-(+)-N,α-dimethylphenethylamine, d-N-methylamphetamine, d-deoxyephedrine, d-desoxyephedrine, 1-phenyl-2-methylaminopropane, d-phenylisopropylmethylamine, methyl-β-phenylisopropylamine, and Norodin), so as to inhibit and/or prevent the use of the ammonia in the reduction of ephedrine/pseudoephedrine to methamphetamine.

2. Description of the Related Art

Of all the drugs of abuse, methamphetamine is the only one so simple to prepare that the individual user can make it independently. It is estimated that 99% of the clandestine laboratories in the United States are involved in the illicit manufacture of methamphetamine. An increasing number of the clandestine methamphetamine laboratories (currently roughly estimated at 20%) use a procedure known as a dissolving metal reduction, Birch reduction, or in the popular literature as the "Nazi" method, of ephedrine or pseudoephedrine commonly extracted from over-the-counter medications. The details for the synthesis are readily available from the open literature and the Internet. Unlike other synthetic drugs, less than 10% of those arrested for the illicit synthesis of methamphetamine are trained chemists.

The relative ease with which methamphetamine is manufactured has led to a proliferation of small-scale "mom and pop" operations. The small-scale labs produce only a small amount of the methamphetamine available in this country. However, clandestine laboratories, often operated by criminally minded individuals untrained in the handling of dangerous chemicals, pose threats of fire, explosion, poison gas, booby traps, and the illegal dumping of hazardous waste. The solvent of choice used for the Nazi synthesis is anhydrous ammonia, often obtained by theft from farmers' supply tanks. The thieves normally pilfer only a few gallons of anhydrous ammonia but too often are the cause of major ammonia spills. Such spills have not only resulted in the loss of thousands of gallons of ammonia for individual farmers, but have resulted in the evacuations of entire towns due to the toxic cloud of ammonia produced.

The handling of anhydrous ammonia is an extraordinarily dangerous activity. The liquid is extremely cold (boiling point, −28° F.) and the vapor is highly volatile. Contact of the liquid with skin or mucus membranes causes a combination of frostbite, direct ammonolysis of the skin by ammonia, and saponification of the epidermal fats by ammonium hydroxide formed by the reaction of ammonia and water. A very real concern is severe injury to children who learn about methamphetamine synthesis from the Internet without knowledge of the risks associated with the handling of anhydrous ammonia.

The small-scale clandestine laboratories are often considered to be more dangerous than the larger scale labs. Smaller scale laboratories suffer from amateur chemists inexperienced in the handling of hazardous chemicals and the consequences of potential accidents. This point is evident from the large number of children present at clandestine laboratories seized in 1999, nearly 870 children were reported to be at the sites with 180 exposed to toxic chemicals and 12 found injured by the chemicals.

The small size of the clandestine methamphetamine labs and the brief time required for the methamphetamine synthesis provide stealth for the laboratories. The required equipment will easily fit into the trunk of a car. The methamphetamine synthesis can be carried out in a hotel room or on the side of the road before disposing of the waste and concealing the laboratory equipment. The Nazi method enjoys the advantage of producing relatively little odor compared with other synthetic methods, greatly minimizing the risk of detection.

The key reagent in the Nazi methamphetamine synthesis is the solvated electron. The solvated electron is a potent reducing agent and is sufficiently long-lived in liquid ammonia that it is useful for synthetic purposes. Dissolving metal reagents, typically alkali and alkaline earth metals, in anhydrous ammonia generates the solvated electron, as follows, using lithium as an example:

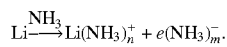

where Li is lithium metal, $NH_3$ is the ammonia solvent, and $Li(NH_3)_n^+$ and $e(NH_3)_m^-$ are the ammonia solvated lithium ion and electron, respectively. The proposed mechanism of the dissolving metal reduction reaction involves the two-electron reduction of ephedrine or pseudoephedrine to give the methamphetamine product, as follows:

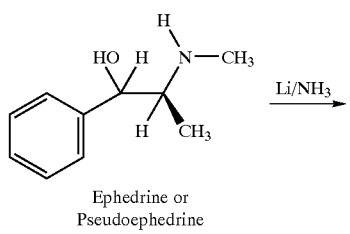

Ephedrine or
Pseudoephedrine

-continued

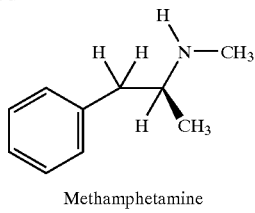

Methamphetamine where the chirality of the carbon center alpha to the phenyl ring is lost during the reduction.

It is an object of the present invention to increase the level of difficulty, time, equipment, and supplies necessary to synthesize methamphetamine by the dissolving metal reduction method. Because the average methamphetamine producer has relatively low chemistry skills, increasing the level of difficulty is expected to significantly decrease the number of individuals capable of conducting the procedure. Additionally, by increasing the time, equipment, and supplies required for the synthesis, the risk of detection of the clandestine laboratory will increase as well.

It is a further object of the invention to provide a method of preventing methamphetamine synthesis from anhydrous ammonia whereby electrons present in the ammonia will react with a chemical reagent in preference over ephedrine and/or pseudoephedrine. By this method, the reagent will interfere with, or eliminate, the ability of electrons to reduce ephedrine and/or pseudoephedrine to methamphetamine.

It is an object of the invention therefore to identify chemical reagents which will react with solvated electrons more efficiently than ephedrine and/or pseudo ephedrine.

SUMMARY OF THE INVENTION

These and further objects of the invention are accomplished by a method of inhibiting or preventing the use of anhydrous ammonia as a solvent in a dissolving metal reduction process which comprises adding to anhydrous ammonia a chemical reagent which is capable of scavenging solvated electrons generated when an alkali or alkaline earth metal is dissolved in the anhydrous ammonia containing the chemical reagent, the chemical reagent being added to the anhydrous ammonia in a methamphetamine synthesis-inhibiting amount, such that when alkali or alkaline earth metal is dissolved in the anhydrous ammonia containing the chemical reagent and thereafter ephedrine and/or pseudoephedrine is introduced to the anhydrous ammonia to produce a reaction product, the methamphetamine yield in the reaction product is below 50%, preferably below 10% and more preferably below 1%.

The chemical reagent utilized in accordance with the invention can be divided into two distinct categories. The first category is a compound capable of undergoing a finite number of one-electron reduction processes. Compounds that exhibit reactivity of this type will be referred to herein as "stoichiometric compounds". Organic chemical compounds and halogenated derivatives thereof typically fall under this category. The disadvantage of this approach is that, in principle, the stoichiometric compounds can be overcome by the addition of excess lithium metal. The second category is a compound that is capable of catalyzing the conversion of the solvated electrons into an unreactive form. Compounds of this class will be referred to as "catalytic compounds". The distinct advantage of catalytic compounds is that it is not, in principle, possible to overcome the catalyst by the addition of excess lithium. The catalyst will simply regenerate itself and consume the excess electrons. Metal ion coordination compounds and organometallic compounds typically fall under this category.

The phrase "methamphetamine synthesis-reducing amount" is defined herein as that quantity of electron scavenging chemical reagent sufficient to reduce the methamphetamine yield from anhydrous ammonia using the dissolving metal reduction process to below about 50%. The term "scavenging" utilized herein refers to the ability of the chemical reagent to preferentially react with solvated electrons relative to ephedrine/pseudoephedrine. "Methamphetamine yield" is obtained from the ratio of ephedrine and methamphetamine present in the reaction product as determined by suitable chromatographic separation. The yield of methamphetamine as a function of additive concentration can be empirically represented by the following relation:

% Methamphetamine Yield=$Y_{min}$+$(Y_{max}-Y_{min})$/(1+exp(($MP-MP_{50}$)/$d(MP)$))

where $Y_{min}$ is the minimum methamphetamine yield obtained at infinite concentration of chemical reagent, $Y_{max}$ is the maximum yield of methamphetamine observed in the absence of chemical reagent, MP is the mole % of chemical reagent relative to lithium, $MP_{50}$ is the mole % of chemical reagent at which 50% quenching is observed, and $d(MP)$ is the derivative with respect to the mole % at $MP_{50}$. The $MP_{50}$ value provides a convenient, quantitative means of comparing the scavenging efficiency of various chemical reagents.

DESCRIPTION OF THE PREFERRED EMBODIMENTS

In the dissolving metal reduction method of methamphetamine synthesis, the ephedrine or pseudo-ephedrine starting ingredient is obtained, often by extraction from over-the-counter cold medication. Anhydrous ammonia is obtained, typically by theft from agricultural supplies. Lithium metal is obtained from lithium batteries. Lithium metal is dissolved in the liquid, anhydrous ammonia to give a blue colored solution, to which ephedrine is added. The ammonia is allowed to boil off leaving the crude, free-base methamphetamine product, which is typically purified by common practice and converted to the hydrochloride salt.

Anhydrous ammonia is a commonly used solvent in chemistry. The properties of anhydrous ammonia are shown in Table 1.

TABLE 1

| Physical Properties of Anhydrous Ammonia | |
|---|---|
| Vapor Pressure: | ~10 atm at 22° C. |
| Normal Boiling Point: | −33° C. |
| Normal Freezing Point: | −78° |
| Dielectric Constant: | ~22 at −34° C. |
| Density: | 0.75 g cm$^{-3}$ at −60° C. |
| Autoprotolysis: | 2$NH_3$ = $NH_4^+NH_2^-$ pK = 32.5 |

Anhydrous ammonia is structurally related to water but has a reduced ability to dissolve ionic compounds due to its lower dielectric constant. The blue color of the solution is due to the solvated electron formed by ionization of the metal, as follows:

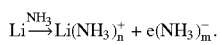

where all species have been previously defined.

The significance to chemists is that a solvated electron is a powerful chemical reagent. The solvated electron is both a strong base and a strong reducing agent.

The solvated electron is stable in ammonia solutions for long periods of time but in the presence of many compounds, it undergoes rapid reaction to yield reduced products. The Nazi methamphetamine synthesis takes advantage of the electron/ammonia solutions in a relatively simple and high yield preparation of the drug that uses readily available starting materials.

A proposed reaction mechanism for the dissolving metal reduction method is as follows:

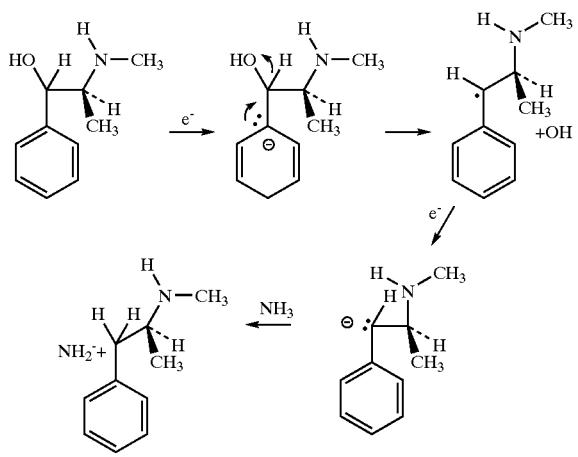

The key to the reaction, and its defeat, is the reaction of the solvated electron with ephedrine or pseudoephedrine. If the solvated electron is consumed by a chemical reagent at a rate significantly higher than its reaction with ephedrine or pseudoephedrine, methamphetamine synthesis will be inhibited or prevented.

A wide range of chemical reagents will react with the highly reactive, strongly reducing, solvated electron in anhydrous ammonia. For convenience, the reagents are divided into two categories: stoichiometric compounds and catalytic compounds. Such compounds can be dissolved in ammonia to create a homogeneous solution, or they may remain undissolved and provide a heterogeneous surface for reaction. The principle of the present invention therefore is that synthesis of methamphetamine from anhydrous ammonia via the dissolving metal reduction method can be effectively inhibited through the introduction of a chemical reagent or mixture thereof into anhydrous ammonia whereby the chemical reagent scavenges solvated electrons generated when alkali metal is dissolved therein. The inventors have demonstrated that the addition of such chemical reagent(s) to anhydrous ammonia can significantly inhibit, and in some cases practically eliminate the production of methamphetamine from the anhydrous ammonia containing the chemical reagent.

Factors which may influence the selection of an individual chemical reagent is the compound's boiling point, the solubility of the compound in ammonia, the effect of the compound on the legitimate use of ammonia by farmers, the amount of compound necessary to achieve the desired result, the cost of the compound, and the impact of the compound on the environment. Choosing a compound which possesses a boiling point close to that of ammonia increases the likelihood that the compound will be carried over during a distillation of the ammonia, thus making removal of the compound from ammonia very difficult. Compounds that are soluble in ammonia will prevent gumming of spray equipment utilized by farmers to apply the ammonia fertilizer to crops. Use of compounds containing micronutrients, e.g., transition metals such as iron or molybdenum, will promote plant growth. Utilizing these criteria, those of ordinary skill in the art can readily identify suitable compounds through routine experimentation.

Stoichiometric Compounds

Stoichiometric compounds are capable of undergoing a finite number of one-electron reduction processes and include organic chemical compounds and halogenated derivatives thereof. The amount of stoichiometric compound added to anhydrous ammonia can range broadly and is dependent upon the number of one-electron reductions that the compound is thermodynamically capable of undergoing. Halogenated compounds are particularly preferred since each halogen atom is theoretically capable of scavenging two electrons. The amount reagent needed, in units of moles, to suppress the methamphetamine yield, i.e., the methamphetamine synthesis-inhibiting amount, is equal to the number of moles of lithium divided by the number of electrons that the reagent is capable of reacting with. The amount of stoichiometric compound utilized will typically range broadly from about $10^{-5}$ to about 0.1 mmol per mL of anhydrous ammonia, preferably from about $10^{-3}$ to about $10^{-2}$ mmol per mL of anhydrous ammonia. Compounds that are acidic in anhydrous ammonia have proven to be effective at inhibiting methamphetamine synthesis when present in high concentration. Preferred organic compounds or halogenated derivatives thereof for use in accordance with the present invention include urea, α-tocopherol (vitamin E) and derivatives thereof, pentamethylchromanol, 1-chloromethyl naphthalene, trichloroethylene, 2-chloro-6-(trichloromethyl)-pyridine and 1,1,1,2-tetrafluoroethane.

Catalytic Compounds

Catalytic compounds accelerate the reaction of electrons with the ammonia solvent to produce the amide anion and hydrogen gas, as follows:

$$2NH_3 + 2e_s^- \xrightarrow{catalyst} 2NH_2^- + H_2$$

The catalyst removes the kinetic stability of the electrons, increasing their rate of reaction with the ammonia solvent. A catalyst is a chemical that increases the rate of a chemical reaction but is not consumed in the reaction and is thus used repeatedly. The amide ion, $NH_2^-$, produced by the catalytic reaction is a weaker base and less powerful reducing agent than the solvated electron and cannot reduce ephedrine/pseudoephedrine. Therefore, the addition of a small amount of the catalyst will render anhydrous ammonia useless to the clandestine drug producers. The methamphetamine synthesis-inhibiting amount of catalytic compound utilized will typically range broadly from about $10^{-9}$ to about 0.1 mmol per mL of anhydrous ammonia, preferably from about $10^{-5}$ to about $10^{-3}$ mmol per mL of anhydrous ammonia. Preferred catalytic compounds include metal coordination compounds, more preferably transition metal coordination compounds such as, for example, Fe(III) compounds including $FeCl_3$, Fe(III) citrate, Fe(acetylacetonate)$_3$, and Fe($F_6$-acetylacetonate)$_3$, Fe(II) compounds including $FeCl_2$ and organometallic compounds such as ferrocene and ferrocene derivatives, such as the ferrocene derivatives described in U.S. Pat. Nos. 4,053,296 and 4,167,405, incorporated by reference herein. Ferrocene is the most preferred organometallic compound.

The invention now will be described with respect to the following examples; however, the scope of the present invention is not intended to be limited thereby.

EXAMPLES

The following general reaction procedure was employed for each of the examples hereinbelow:

Anhydrous ammonia gas was condensed in a 25 mL schlenk tube immersed in a dry ice/isopropanol bath to a volume of 10 mL of liquid ammonia. The chemical reagent was added, either neat or as a THF solution, with magnetic stirring. Lithium metal, ca. 29 mg was added to the liquid ammonia producing a dark blue solution. THF, 1 mL, was added as a cosolvent. A solution of (1R,2S)-(-)-ephedrine, 100 mg dissolved in 1 mL dry THF, was added dropwise to the blue ammonia solution with magnetic stirring. The reaction mixture was allowed to stir for ca. 10 min. after ephedrine addition was complete before excess solid $NH_4Cl$ was added to quench the reaction. The reaction mixture was then allowed to warm to ambient temperature and the ammonia allowed to boil off. The resulting residue was partitioned between 10 mL water and 10 mL diethyl ether. The aqueous layer was further extracted with 2×20 mL diethyl ether. The combined ether layers were dried over $MgSO_4$ and the ether evaporated to give a clear oil. Analysis of the product was carried out by TLC (silica,. $CHCl_3$/EtOH/$NH_4OH$, 88:10:2) and GC-MS using authentic standards. The yields were evaluated from chromatographic separation using the ratio of methamphetamine to ephedrine. No significant side products were identifed in the reactions investigated.

The data in Table 2 below identify the chemical reagents used for each example, amount of chemical reagent used and the methamphetamine yield.

Each of the reagents set forth below were obtained commercially and were of the highest purity available, except for iron(III) 1,1,1,5,5,5-hexafluoro acetylacetonates, (iron(III) 1,1,1,5,5,5-hexafluoro-2,4-pentanedionate) which were synthesized as follows: Iron(III) chloride hexahydrate (2.162 g, 8.000 mmol) was dissolved in water (15 mL), resulting in a yellow-orange solution, and stirred at rome temperature. Neat 1,1,1,5,5,5-hexafluoro-2,4-pentanedione (5.000 g, 24.00 mmol) was added dropwise to the stirring solution and the color immediately turned red. After stirring for 15 minutes, product began to separate as a dark solid. Stirring was continued for another 2 hrs when product ceased to form. Filtration, washing with water (~15 mL) and drying under vacuum gave crude product as an orange-brown solid. Recrystallization from aqueous ethanol gave 217 mg of purified product as a brick-red solid (mp. 110° C. [dec.]). Yield: 0.319 mmol, 4.0%.

The amounts of each chemical reagent set forth in Table 2 are expressed as a mol % relative to the amount of lithium added. The methamphetamine synthethic yield values in Table 2 are expressed as a percentage of the methamphetamine/ephedrine ratio.

TABLE 2

| Example No. | Chemical Reagent | Amount of Chemical Reagent | Methamphetamine Yield |
|---|---|---|---|
| 1 | Urea | 23% | 37% |
| 2 | α-Tocopherol | 14% | 1% |
| 3 | 1-chloromethyl naphthalene | 14% | 1% |
| 4 | trichloroethylene | 14% | 1% |
| 5 | 2-chloro-6-(trichloromethyl)-pyridine | 10% | 31% |
| 6 | 1,1,1,2-tetrafluoroethane | 10% | 5% |
| 7 | $FeCl_3$ | 1.0% | 19% |
| 8 | $FeCl_3 + H_2O$ | 1.0% | 3% |

TABLE 2-continued

| Example No. | Chemical Reagent | Amount of Chemical Reagent | Methamphetamine Yield |
|---|---|---|---|
| 9 | $FeCl_2$ | 1.0% | 0% |
| 10 | Fe(III)citrate | 1.2% | 0% |
| 11 | $Fe(acac)_3$ | 0.1% | 0% |
| 12 | $Fe(F_3\text{-acac})_3$ | 0.1% | 0% |
| 13 | $Fe(F_6\text{-acac})_3$ | 0.1% | 0% |
| 14 | Ferrocene | 0.1% | 31% |

It can readily be seen from the data in Table 2 that the incorporation of an electron scavenger in anhydrous ammonia significantly inhibits the production of methamphetamine from the anhydrous ammonia.

Several reactions were studied in sufficient detail to evaluate $MP_{50}$ values, i.e., the amount of additive, relative to the amount of lithium metal, at which the methamphetamine yield is reduced to 50%. These results are listed in Table 3.

TABLE 3

| Example | Additive | $MP_{50}$/mol %  [a] |
|---|---|---|
| 15 | 2-chloro-6-(trichloromethyl) pyridine | 9.22 ± 0.9 |
| 16 | 1,1,1,2-tetrafluoroethane | 7.1 ± 0.2 |
| 17 | Iron(III) Citrate | 0.8 ± 0.08 |
| 18 | Ferrocene | 0.055 ± 0.007 |

[a] The $MP_{50}$ value is an estimate of the amount of additive needed to reduce the methamphetamine yield by 50%, where the amount is given in mol % relative to lithium metal. The errors quoted for examples 15 and 17 are rough estimates, whereas the errors quoted for examples 16 and 18 represent the 95% confidence interval.

Examples 15 and 16 are halogenated organic compounds that can be classified as stochiometric reagents. It can reasonably be expected that halogenated organic molecules will react with two electrons for each halogen atom the molecule possess, and this assumption is consistent with the observed yields. The two iron compounds are catalytic compounds. Fe(III) citrate is capable of scavenging ≧80 electrons and ferrocene was observed to scavenge ≧1000 electrons. The efficiency of ferrocene as a catalyst for the inhibition of methamphetamine synthesis is remarkable. Ferrocene has been found to be soluble in ammonia at the concentration needed for activity, i.e., $4 \times 10^{-4}$ M. Ferrocene has proven to be potent inhibitor, reducing the methamphetamine yield to near zero at concentrations as low as 0.1 mol % relative to lithium, or $4 \times 10^{-4}$ mmol/mL ammonia.

What is claimed is:

1. A method of inhibiting or preventing the use of anhydrous ammonia as a solvent in a dissolving metal reduction process which comprises:

adding to anhydrous ammonia a chemical reagent which is capable of scavenging solvated electrons generated when an alkali or alkaline earth metal is dissolved in the anhydrous ammonia containing the chemical reagent, the chemical reagent being added to the anhydrous ammonia in a methamphetamine synthesis-inhibiting amount, such that when alkali or alkaline earth metal is dissolved in the anhydrous ammonia containing the chemical reagent and thereafter ephedrine and/or pseudoephedrine is introduced to the anhydrous ammonia to produce a reaction product, the methamphetamine yield in the reaction product is below 50%.

2. The method of claim 1 wherein the methamphetamine yield is below 10%.

3. The method of claim 1 wherein the methamphetamine yield is below 1%.

4. The method of claim 1 wherein the chemical reagent is a stoichiometric compound capable of undergoing a finite number of one-electron reduction processes.

5. The method of claim 4 wherein the stoichiometric compound is an organic compound or halogenated derivative thereof.

6. The method of claim 5 wherein the organic chemical compound or halogenated derivative thereof is selected from the group consisting of urea, α-tocopherol, pentamethylchromanol, 1-chloromethyl naphthalene, trichloroethylene, 2-chloro-6-(trichloromethyl)-pyridine and 1,1,1,2-tetrachloroethane and mixtures thereof.

7. The method of claim 5 wherein the organic compound or halogenated derivative thereof is 2-chloro-6-(trichloromethyl)-pyridine.

8. The method of claim 5 wherein the organic compound or halogenated derivative thereof is 1,1,1,2-tetrafluoroethane.

9. The method of claim 1 wherein the chemical reagent is a catalytic compound which reacts with solvated electrons in a catalytic process that removes the kinetic stability of the solvated electrons causing the solvated electrons to undergo rapid reaction to yield reduced products thereby removing the solvated electrons.

10. The method of claim 9 wherein the catalytic compound accelerates the reaction of the solvated electrons with ammonia to produce a reaction product containing amide anion and hydrogen gas.

11. The method of claim 9 wherein the catalytic compound is selected from the group consisting of metal ion coordination compounds and organometallic compounds.

12. The method of claim 11 wherein the metal ion coordination compound is a transition metal ion coordination compound.

13. The method of claim 11 wherein the metal ion coordination compound is a Fe(III) compound.

14. The method of claim 13 wherein the Fe(III) compound is selected from the group consisting of $FeCl_3$, Fe(III)citrate, Fe(acetylacetonate)$_3$ and Fe($F_6$-acetylacetonate)$_3$.

15. The method of claim 11 wherein the metal ion coordination compound is a Fe(II) compound.

16. The method of claim 15 wherein the Fe(II) compound is $FeCl_2$.

17. The method of claim 11 wherein the organometallic compound is ferrocene or a derivative of ferrocene.

18. The method of claim 1 wherein the chemical reagent is ferrocene and the methamphetamine yield is reduced to below 1%.

19. A method of inhibiting or preventing the use of anhydrous ammonia as a solvent in a dissolving metal reduction process which comprises:
adding to anhydrous ammonia a catalytic compound which reacts with solvated electrons generated when an alkali or alkaline earth metal is dissolved in the anhydrous ammonia in a catalytic process that converts the solvated electrons into an unreactive form, the catalytic compound being added to the anhydrous ammonia in a methamphetamine synthesis-inhibiting amount such that when alkali or alkaline earth metal is dissolved in the anhydrous ammonia containing the catalytic compound and thereafter ephedrine and/or pseudoephedrine is introduced to the anhydrous ammonia to produce a reaction product, the methamphetamine yield in the reaction product is below 50%.

20. The method of claim 19 wherein the methamphetamine yield in the reaction product is reduced to below 10%.

21. The method of claim 19 wherein the catalytic compound is a metal ion coordination compound.

22. The method of claim 19 wherein the catalytic compound is an organometallic compound.

23. The method of claim 21 wherein the metal ion coordination compound is a transition metal ion coordination compound.

24. The method of claim 21 wherein the metal ion coordination compound is a Fe(II) compound.

25. The method of claim 24 wherein the Fe(III) compound is selected from the group consisting of $FeCl_3$, Fe(III)citrate, Fe(acetyl acetonate)$_3$ and Fe($F_6$-acetylacetonate)$_3$.

26. The method of claim 21 wherein the metal ion coordination compound is a Fe(II) compound.

27. The method of claim 26 wherein the Fe(II) compound is $FeCl_2$.

28. The method of claim 22 wherein the organometallic compound is ferrocene or a derivative of ferrocene.

29. A method of inhibiting or preventing the use of anhydrous ammonia as a solvent in a dissolving metal reduction process which comprises:
adding to anhydrous ammonia a stoichiometric compound which is capable of undergoing a reaction with solvated electrons generated when an alkali or alkaline earth metal is dissolved in the anhydrous ammonia, the stoichiometric compound being added to the anhydrous ammonia in a methamphetamine synthesis-inhibiting amount such that when alkali or alkaline earth metal is dissolved in the anhydrous ammonia containing the stoichiometric compound and thereafter ephedrine and/or pseudoephedrine is introduced to the anhydrous ammonia to produce a reaction product, the methamphetamine yield in the reaction product is below 50%.

30. The method of claim 29 wherein the methamphetamine yield in the reaction product is reduced to below 10%.

31. The method of claim 29 wherein the stoichiometric compound is an organic compound or halogenated derivative thereof.

32. The method of claim 31 wherein the organic chemical compound or halogenated derivative thereof is selected from the group consisting of urea, α-tocopherol, pentamethylchromanol, 1-chloromethyl naphthalene, trichloroethylene, 2-chloro-6-(trichloromethyl)-pyridine and 1,1,1,2-tetrachloroethane and mixtures thereof.

33. The method of claim 31 wherein the organic compound or halogenated derivative thereof is 2-chloro-6-(trichloromethyl)-pyridine.

34. The method of claim 31 wherein the organic compound or halogenated derivative thereof is 1,1,1,2-tetrafluoroethane.

* * * * *

UNITED STATES PATENT AND TRADEMARK OFFICE
CERTIFICATE OF CORRECTION

PATENT NO. : 6,852,891 B2　　　　　　　　　　　　　　　　　　　　　Page 1 of 1
DATED : February 8, 2005
INVENTOR(S) : George M. Murray et al.

It is certified that error appears in the above-identified patent and that said Letters Patent is hereby corrected as shown below:

<u>Title page, Item [54] and Column 1, line 2,</u>
Title, delete "METAHPHETAMINE" and insert -- METHAMPHETAMINE --

<u>Column 10,</u>
Line 18, delete "(II)" and insert -- (III) --

Signed and Sealed this

Twenty-fourth Day of May, 2005

JON W. DUDAS
*Director of the United States Patent and Trademark Office*